United States Patent [19]

Shirasawa

[11] Patent Number: 5,337,139
[45] Date of Patent: Aug. 9, 1994

[54] MULTICHANNEL OPTICAL MEASURING SYSTEM

[75] Inventor: Yoshiaki Shirasawa, Tsuchiura, Japan

[73] Assignee: Kowa Company Ltd., Japan

[21] Appl. No.: 866,751

[22] Filed: Apr. 10, 1992

[30] Foreign Application Priority Data

May 27, 1991 [JP] Japan .................. 3-120548

[51] Int. Cl.$^5$ .................. G01N 21/59; G01N 21/64
[52] U.S. Cl. .................. 356/73; 356/417; 356/418; 356/414; 250/461.1
[58] Field of Search .......... 356/73, 317, 318, 409–411, 356/414, 416, 417, 418, 419; 250/458.1, 459.1, 461.1, 461.2

[56] References Cited

U.S. PATENT DOCUMENTS

4,738,534  4/1988  Houseman et al. .................. 356/414

FOREIGN PATENT DOCUMENTS

| 184844 | 10/1984 | Japan | 356/73 |
| 273435 | 11/1987 | Japan | 356/418 |
| 195232 | 8/1990 | Japan | 356/418 |
| 2014305 | 8/1979 | United Kingdom | 356/409 |

OTHER PUBLICATIONS

Karjalainen et al, *Journal of Physics E*, vol. 7, No. 4 Apr. 1974, pp. 241–243.

*Primary Examiner*—F. L. Evans
*Attorney, Agent, or Firm*—Bruce L. Adams; Van C. Wilks

[57] ABSTRACT

A multichannel optical measuring system for measuring optical responses of samples illuminated by light of differing wavelengths has a plurality of measurement sample cuvettes each contain a sample to be measured. A first single light source provides a first illumination light. A plurality of sets of optical fibers direct the first illumination light from the first single light source to illuminate, along an optical axis, the samples contained in respective sample cuvettes. A second light source is provided for illuminating each respective sample cuvette with a second illumination light for measuring an intensity of transmitted light through the sample. The optical axis of the second illumination light is perpendicular to the optical axis of the first illumination light. A common photosensor disposed on the optical axis of the second light source measures the intensity of the first illumination light and the intensity of the transmitted light from each sample. Thus, the multichannel optical measuring system can simultaneously measure both the intensity of a first illumination light from a single light source, and the intensity of light transmitted through each sample, for a plurality of samples.

20 Claims, 5 Drawing Sheets

MULTICHANNEL OPTICAL MEASURING SYSTEM

BACKGROUND OF THE INVENTION

1. Field of the Invention

This invention relates to a multichannel optical measuring system, more particularly to a multichannel optical measuring system for measuring the optical response of a sample illuminated by light.

2. Description of the Prior Art

In recent years fluorochromes that have been developed are being used for quantitative measurement of calcium ions, magnesium ions and the like in various types of blood cells. However, systems now in use for measuring fluorescent and transmitted light are single channel systems for making measurements relating to just one sample or for measuring the optical response obtained with an incident light beam of just one wavelength.

However, such single channel systems cannot be used when a large number of samples have to be measured in a short space of time, such as for measurements relating to floating cells in the blood such as platelets, leukocytes and lymphocytes, with the aim of measuring changes in the calcium ion or magnesium ion content of blood platelets, for example, while at the same time measuring changes in the aggregation of such cells.

To provide a conventionally configured system with multichannel fluorometry capabilities would involve the addition of as many light sources as there are sample (measurement) cuvettes to be measured, and the corresponding optical systems for condensing the light from these sources and selecting wavelengths. The only way to do this would be to use an array of conventional single channel systems, which would result in an impractically large and costly arrangement.

Then there is the fact that fluorometry involves the use of costly high-voltage mercury or xenon lamps, and each optical system needs to have a switchover unit to switch among diffraction gratings or interference filters for measuring fluorescent intensities obtained at multiple wavelengths. The ability to measure changes in a cell's fluorescent intensity while at the same time measuring the intensity of the light transmitted by the cell enables the chemical composition of the cell to be determined from the spectral absorption characteristics and the shape of the cell to be determined from the scattered light. When studying cell physiology and pharmacological effects, such data is useful by enabling the relationships among the various parameters to be ascertained.

However, measurement systems based on conventional technology make simultaneous use of two photosensors, one being a photomultiplier that is used as the fluorescent photosensor and the other being a photodiode that is used as the transmitted light photosensor. Moreover, the beam of illumination used for measurement of fluorescence and the beam of illumination used for measurement of transmitted light are both projected along the same optical path to the measurement cuvette, a configuration that is not suitable for multichannel measurements. In addition, to implement the conventional system arrangement, in which a photomultiplier is used as a photosensor to facilitate measurement of the weak fluorescence, requires a large light-receiving section disposed near the measurement cuvette. In the case of a multichannel system having multiple measurement cuvettes, such an arrangement using photomultipliers as the photosensors would again be too bulky and costly.

SUMMARY OF THE INVENTION

An object of the present invention is therefore to provide a light, compact, simple and low-cost multichannel optical measuring system that is capable of simultaneously measuring the intensity of fluorescence and transmitted light of a plurality of samples.

In accordance with the present invention, the above object is achieved by a basic system arrangement whereby light from a single light source is directed through a condenser lens, and then through a multiple interference filter arrangement in which filters can be selected to select light of a prescribed wavelength, and the light of the selected wavelength is then directed along multiple branches of a quartz optical fiber and is thereby projected at glass cuvettes that each contain biological cell samples.

The tip of each of these optical fiber branches is arranged in the vicinity of a glass cuvette. Use of this multibranch optical fiber arrangement makes it possible to irradiate multiple glass cuvettes by means of a first single light source and its appurtenant optical system, thereby achieving a measurement system that is smaller and more resource-efficient. As the optical fibers are flexible and the tip of each is no more than 5 mm across, it is possible to arrange multiple measurement cuvettes close together, which also helps to reduce the size of the system.

To ensure that all of the measurement cuvettes receive the same uniform level of a first illumination light from the light source, the multibranch optical fiber arrangement is comprised of a randomly-divided bundle of several hundred optical fibers. For measurement purposes, the level of background light is reduced using a bundle filler that blocks fluorescent light.

A round glass sample cuvette is used for measurements. To minimize loss of the light passing through the glass, the light from the optical fibers is collimated and passed through an iris. This decreases background light during measurements and thereby improves measurement accuracy. Round glass cuvettes are much cheaper than square quartz cuvettes, making them suitable for use as the measurement cuvettes of a multichannel measurement system.

The intensity of transmitted light is measured using a light-emitting diode as a second light source arranged at right-angles to the optical axis of the first illumination light used for measuring fluorescence. A photodiode photosensor is disposed on the optical axis of light emitted by the light-emitting diode and at right-angles to the optical axis of the light brought by the optical fiber, with a single photodiode photosensor being used to measure the fluorescence intensity and transmitted light intensity. A photodiode photosensor provides adequate measurement capability for measuring the fluorescence of a multiplicity of cells in a measurement cuvette. The optical fibers positioned in the vicinity of the measurement cuvettes to be illuminated by light projected by the optical fibers, and the light-emitting diodes and photodiode photosensors, are all small, which enables multiple measurement cuvettes to be placed close together and thereby reduce the size of the system.

An appropriate selection of interference filter is made to cause the cells to be irradiated with excitation light of a prescribed wavelength, while at the same time the light-emitting diodes are energized so that they emit light at the same time the excitation light is being interrupted so as to effect simultaneous photodiodic measurement, in the form of a time-series, of the fluorescent and transmitted light intensities of multiple samples. Thus, it is possible to simultaneously measure the fluorescence, light absorption and scattered light of cells. In accordance with the above-described system configuration, therefore, it is possible to carry out simultaneous multichannel measurement of the intensity of fluorescent/transmitted light of multiple samples irradiated with light of different wavelengths.

BRIEF DESCRIPTION OF THE DRAWINGS

The purposes and features of the present invention will become more apparent from a consideration of the following detailed description taken in conjunction with the accompanying drawings in which.

DETAILED DESCRIPTION OF THE PREFERRED EMBODIMENTS

The invention will now be described in detail on the basis of the preferred embodiment illustrated in the drawings.

Figure 1:
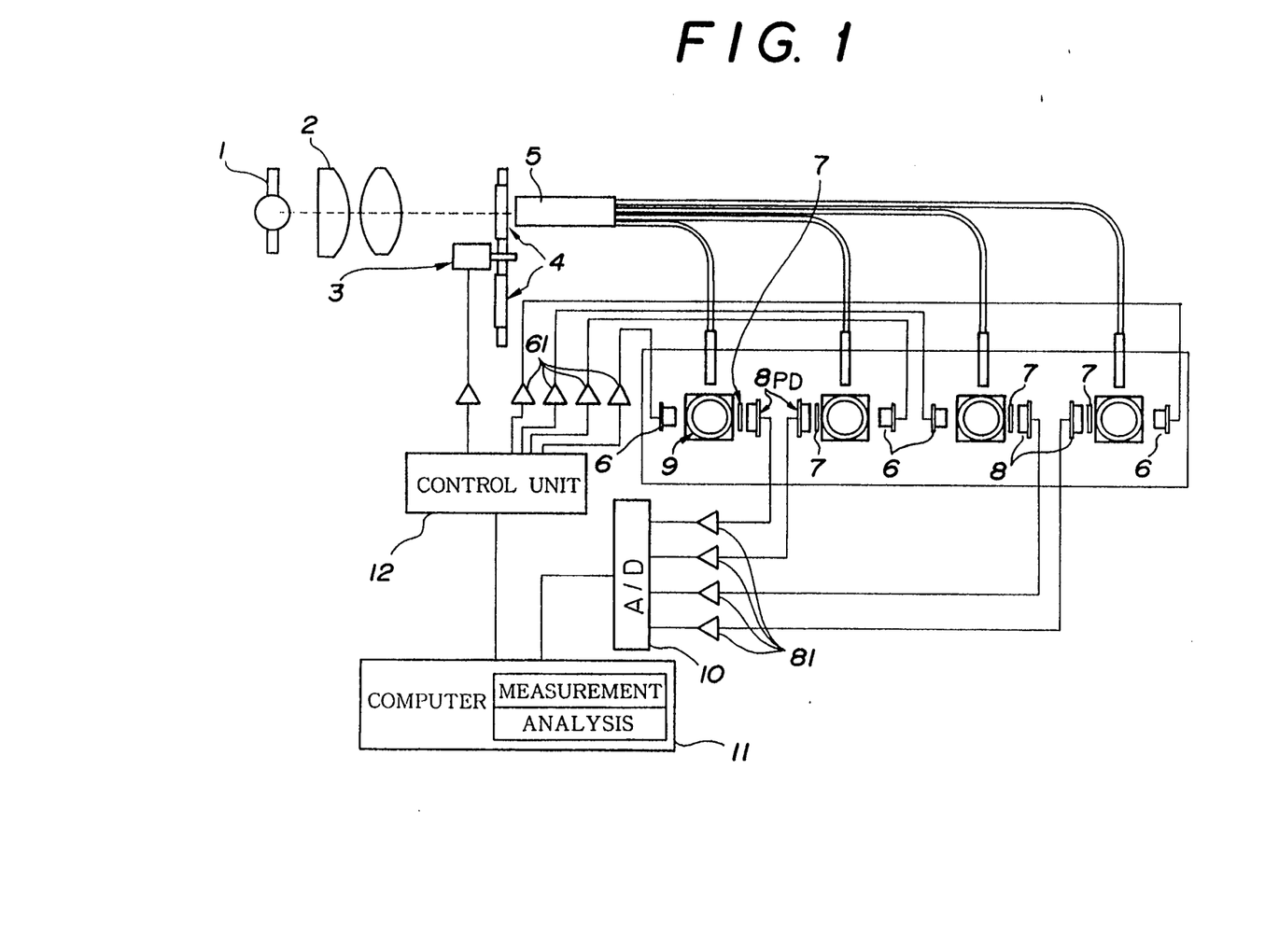
FIG. 1 is a diagram for explaining the structure of the multichannel optical measuring system of the present invention.

FIG. 1 shows the structural arrangement of a system incorporating the present invention for the simultaneous four-channel measurement of fluorescent and transmitted light. A beam of light from a xenon lamp light source 1 is used to measure the intensity of fluorescent light. The beam of light from the xenon light source 1 is condensed by a set of quartz lenses 2, and is then passed through an interference filter 4 to obtain light of a prescribed wavelength which then impinges on a set of quartz optical fibers 5.

The interference filter 4 has a rotatable disk having a plurality of filter elements with different characteristics. A filter switching unit 3, under the control of a control unit 12, enables any particular interference filter element to be selected and the timing of the light incident on the optical fibers 5 to be controlled. The filter switching unit 3 consists of a DC motor and a photointerrupter or the like for detecting the position of the filter elements. The non-filter portions of the disk of the interference filter 4 are utilized to control the timing of the light impinging on the set of optical fibers 5.

Figure 2:
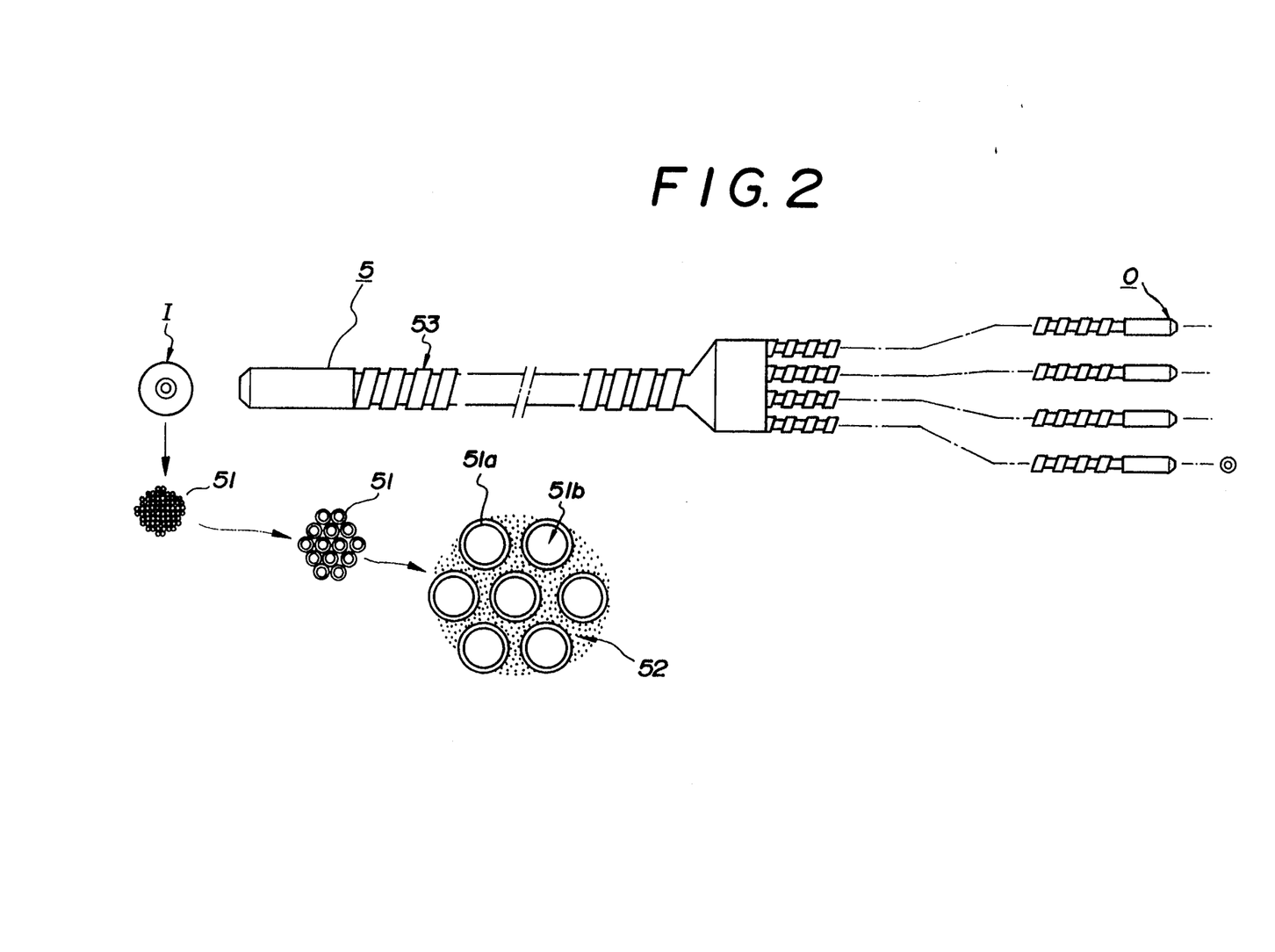
FIG. 2 is a diagram for explaining the quartz optical fiber arrangement used in the system of FIG. 1.

With reference to FIG. 2, the set of quartz optical fibers 5 is constituted as bundle of some 300 quartz fibers 51, each of which has a core with a diameter of approximately 150 $\mu$m. Background light during measurements is reduced by using a filler 52 that does not transmit fluorescent light. The incident end portion I of each of the fibers of the bundle faces towards the xenon light source 1. Reference numerals 51a and 51b denote the cladding and core, respectively, of each quartz fiber 51.

To ensure that the light from the light source illuminates each measurement cuvette with the same intensity, at an intermediate point or at a point near the exit end portion O the quartz fibers 51 are randomly divided into four bundles of about 75 fibers each. The collective exit end portion O of each bundle is disposed facing one of four corresponding round sample measurement cuvettes 9 made of glass that are detachably inserted into the system apparatus (FIG. 1).

The optical fibers 5 are used to irradiate the sample measurement cuvettes 9 with ultraviolet (UV) excitation light. For simultaneously measuring the intensity of light transmitted by samples in the sample measurement cuvettes 9, each of the cuvettes 9 is provided with a light-emitting diode (LED) 6, an interference filter 7 and a photodiode 8. The arrangement around each of the sample measurement cuvettes 9 is shown in detail in FIG. 3. UV excitation light from the optical fibers 5 is projected at the cuvette 9 after being collimated by a lens 10' and passing through an iris 11' to reduce stray light components being picked up through the glass of the cuvette 9.

Figure 3:
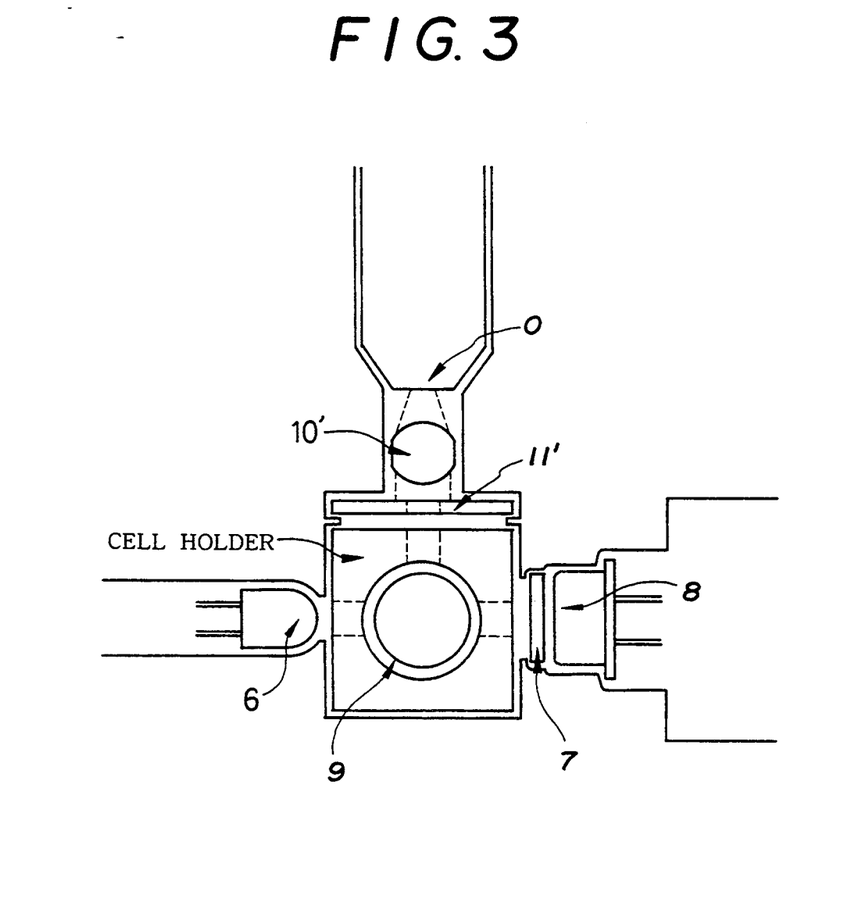
FIG. 3 is a diagram for explaining the structure of the illumination system, light receiving section and measurement cuvette.

The LED 6 used as the light source for measuring the intensity of transmitted light is arranged facing the measurement cuvette 9 at right-angles to the optical axis of the light from the optical fibers 5. Fluorescent and transmitted light is detected by the photodiode 8 which is arranged facing the cuvette 9 at right-angles to the optical axis of the light from the optical fibers. The interference filter 7 is provided at the front of the light-receiving face of the photodiode 8, as required, to select a particular fluorescent light wavelength.

A driver 61 and the control unit 12 are used to synchronize the switching on of the LED 6 with the selection of the interference filter 4 by the filter switching unit 3 or with the interruption of the light beam to the optical fibers. The amount (intensity) of light received by each of the photodiodes 8 is converted into a corresponding electrical signal that is input to a personal computer 11 via a SCSI, GPIB or other suitable interface after being amplified by an amplifier 81 and subjected to analog/digital (A/D) conversion by an A/D converter 10. The measurement cuvettes 9 are also connected to the personal computer 11 by a suitable interface means.

Figure 4:
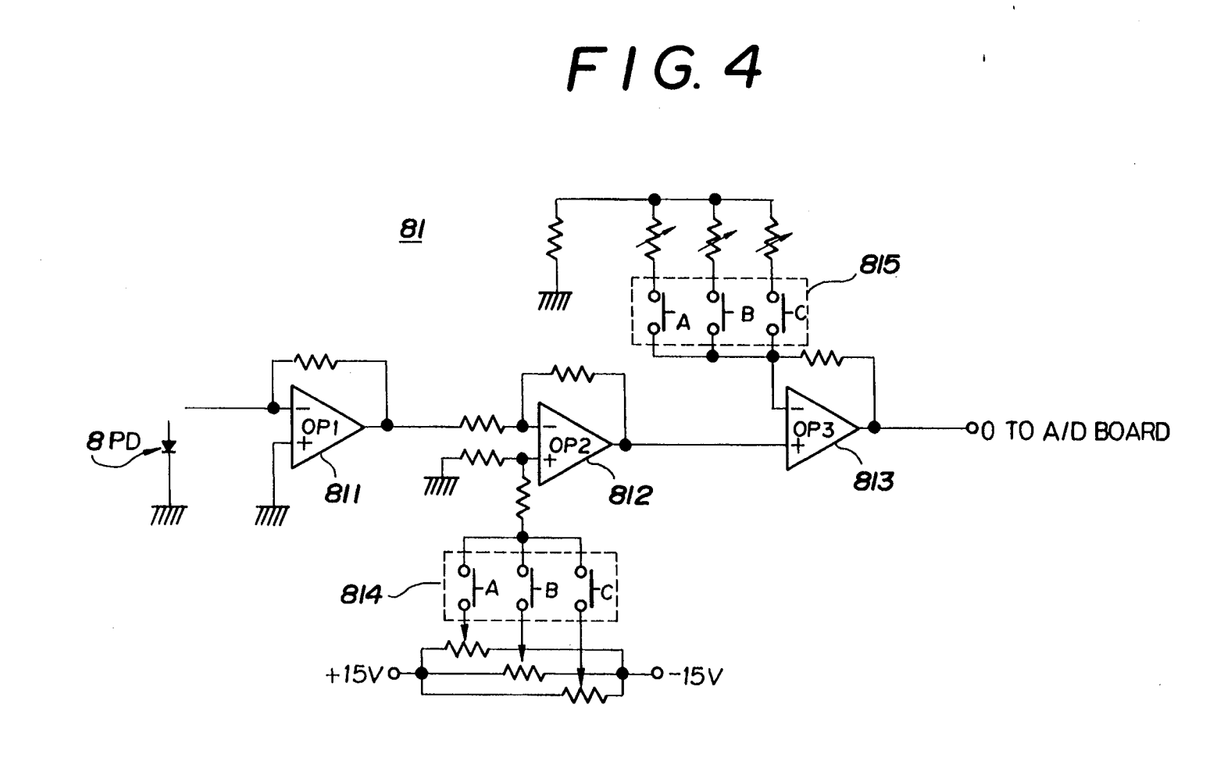
FIG. 4 is a circuit diagram of the amplifier of the light receiving section.

In most cases there are considerable differences in the intensity levels of fluorescent and transmitted light received by photodiodes, and in the intensity levels of the background light. To improve the signal/noise (S/N) ratio, as shown by FIG. 4 the amplifier 81 is constituted by three operational amplifier stages 811 to 813. The amplification factors of amplifiers 812 and 813 are arranged so that background light may be compensated for by the switching of offset voltages and amplifications based on control signals A, B, and C synchronized, respectively, with the switching of interference filter 4, interference filter 7, and pulses of light emitted by LED 6.

A Peltier element and thermistor arrangement (not shown) is used for temperature maintenance of the measurement cuvettes 9, and a magnetic stirrer is provided beneath the measurement cuvettes to stir the cells and solution in the measurement cuvettes.

The personal computer 11 is used to control interference filter 4 selection and, via control of the LED 6, UV excitation light and transmitted light, and is also used to measure the transmitted light and the fluorescent light produced by samples in the measurement cuvettes 9 based on the input from the A/D converter 10 of the amount of light received by the photodiode 8. The personal computer 11 contains software stored in memory and in secondary storage means for performing measurements and analyzing measured quantities. After measurement data is sampled and processed by the analysis software it is output to an output device such as a display monitor, printer or plotter.

The procedure used for simultaneously measuring the aggregation ability and calcium ion concentration of rabbit blood platelets will now be described.

In accordance with a standard procedure, blood containing citric acid is centrifuged to obtain washed blood platelets. These platelets are then incubated for 20 minutes in a nutrient solution that includes the fluorochrome fura-2 AM. This is followed by a centrifuging operation to enable the platelets to be washed in a nutrient solution that does not include fura-2 AM.

The suspension of platelets carrying fura-2 fluorochrome thus prepared is put in a measurement cuvette 9 which is then placed into position in the system apparatus, and stirring by magnetic stirrer is started. At the same time, 340 nm and 380 nm interference filters are switched while the LED is operated sequentially for periods of one second at a time, for example, to produce an input of fluorescent and transmitted light intensity signals obtained via the photodiode.

After the elapse of the prescribed measurement period, a measurement cuvette 9 containing platelets not carrying fura-2 is placed into the system apparatus, the 340 nm and 380 nm interference filters are switched and the same procedure is used to obtain an input of each background fluorescent light intensity. A measurement cuvette 9 containing only the nutrient solution is exposed to light from the LED to input the intensity of totally transmitted light.

The entire sequence of operations described above is controlled by the light measurement software of the personal computer 11 that has been specifically prepared for this system. The user performs the operations in accordance with directions displayed on a display monitor or the like.

Sampling data relating to the intensity levels of fluorescent and transmitted light obtained during the measurement periods via the A/D converter 10 is stored on magnetic storage media or the like by the personal computer 11. The analysis software uses this data to calculate the calcium ion concentration and aggregation performance of the target platelets, and displays or prints out the results. One possible output format is shown by FIG. 5 in which the calcium concentration and aggregation data during the prescribed measurement period are plotted against elapsed time.

The analysis software obtains the ratio of the intensities of the fluorescent light from platelets carrying fura-2 resulting from 340 nm and 380 nm excitation light after subtracting the background light. This can be treated as a value having a correlation to the calcium ion concentration of the cells. Agglutination performance of the platelets is indicated by changes in transmissivity.

The above measurement can be carried out with respect to all of the measurement cuvettes 9 of the apparatus. For example, it is possible to perform simultaneous measurements when the measurement cuvettes 9 each contain different samples, or to perform measurements relating to platelets with/without fura-2 and to simultaneously measure the intensity of totally transmitted light using just the nutrient solution.

Figure 5A:
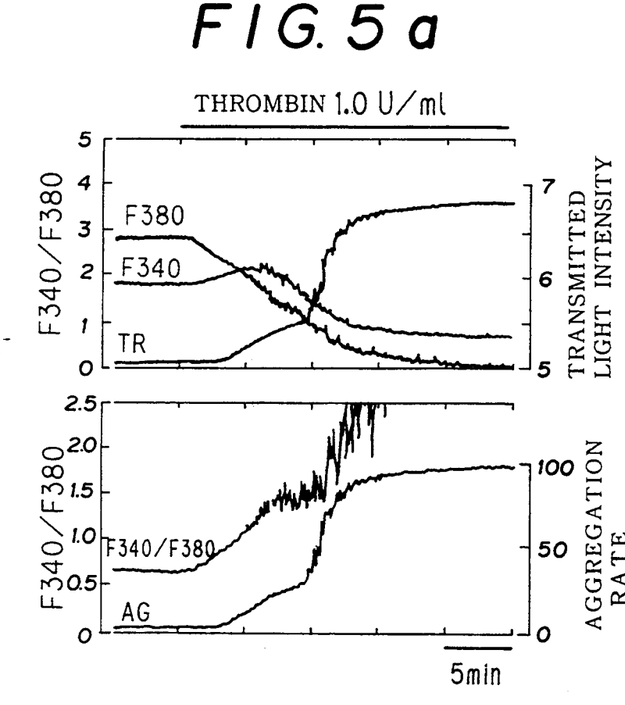
FIGS. 5A and 5B are a set of graphs representing the results of measurements of cell aggregation and changes in cellular calcium ion concentrations in rabbit platelets carrying a calcium-ion-sensitive fluorochrome stimulated by collagen and thrombin.
Figure 5B:
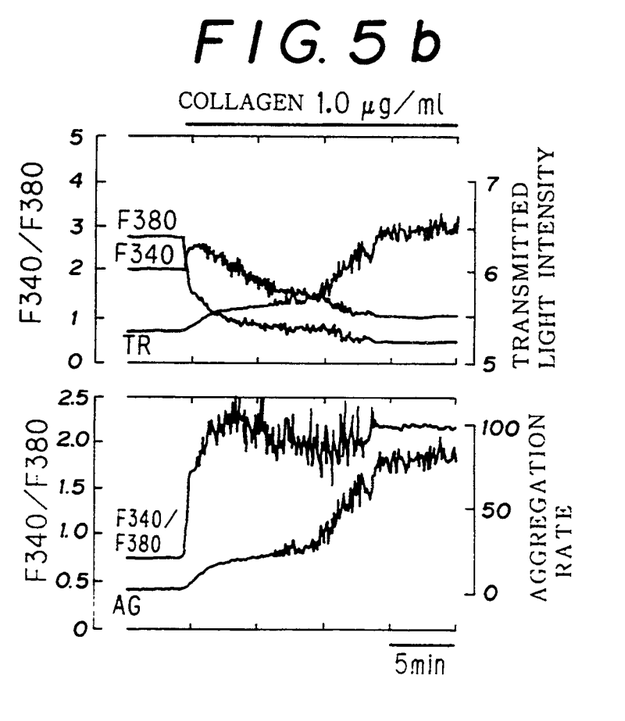

FIG. 5 shows the results of measurement and analysis of calcium ions when thrombin and collagen were used to induce platelet aggregation. Specifically, using rabbit platelets carrying the calcium-ion-sensitive fluorochrome fura-2, FIG. 5 shows measured values of changes in calcium ion concentration and aggregation performance induced by thrombin (FIG. 5A) and collagen (FIG. 5B). F340 and F38 denote fluorescent intensity produced by excitation with 340 nm and 380 nm light, respectively, TR denotes transmitted light intensity, F340/F380 denotes the ratio of fluorescent light intensities related to cell calcium ion concentrations, and AG denotes the aggregation ratio obtained from the ratio of fluorescent light intensities.

FIG. 5A shows that the effect of thrombin was to produce large platelet aggregations, thereby reducing the numbers of cells impinged upon by the excitation light and therefore greatly reducing the intensity of the fluorescent light, making it impossible to measure the calcium ions. As seen from FIG. 5B, however, with the medium degree of aggregation produced using collagen, adequate measurement was possible.

This shows that in accordance with this embodiment changes in the intensity of fluorescent light from samples in a plurality of cuvettes can be measured using an arrangement comprising directing light from a single light source through condensing means and a wavelength-selection optical system and using multiple optical fibers to project this light at the target cells. As this objective of measuring fluorescent light intensities of a plurality of samples is achieved using a single optical system, the measurement apparatus is compact and resource-efficient.

The light from the optical fibers 5 is projected at the cuvette 9 after being collimated by a lens 10' and passed through an iris 11' to reduce autofluorescence and stray light from the round glass measurement cuvettes 9, enabling high-precision measurements to be carried out. Using round glass cuvettes 9 is simple and economical.

By enabling the measurement cuvettes to be placed in closer proximity, using photodiodes as the photosensors enables the size of the system apparatus to be decreased. Both fluorescent and transmitted light can be measured with a single photodiode by arranging the photodiode on the optical axis of the light emitted by the light-emitting diode at right-angles to the optical axis of the light from the optical fibers. Also, it is possible to measure the intensity of fluorescent light while at the same time measuring the intensity of transmitted light. The chemical composition of a sample can be determined on the basis of changes in the fluorescence and at the same time the shape of the cell can be determined on the basis of changes in the transmitted light, making this a valuable tool for physiological, medical and pharmacological research.

The apparatus according to this invention is particularly suited to measurements relating to floating cells in the blood such as platelets, leukocytes and lymphocytes. For example, it can be used to measure changes in calcium ion and magnesium ion levels in blood platelets while at the same time measuring changes in the aggregation performance of such cells, and to ascertain the relationship between the two.

The system apparatus of this invention is ideal for applications in which it is necessary to measure large numbers of such cell samples in a short space of time. The arrangement described above is used to measure fluorescent and transmitted light intensities of multiple samples. However, the same optical system may be used for simultaneous measurement of cell fluorescence and light absorption or light scattering.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A multichannel optical measuring system for measuring optical responses of samples illuminated by light of differing wavelengths, comprising: a plurality of measurement sample cuvettes each for containing a sample to be measured; a first single light source for providing a first illumination light; multibranch optical fiber means comprising a plurality of sets of optical fibers, each set being effective to direct the first illumination light from the first single light source to illuminate along an optical axis the sample contained in a respective sample cuvette; second light source means for illuminating each respective sample cuvette with a second illumination light for measuring an intensity of transmitted light through the sample, the optical axis of the second illumination light being perpendicular to the optical axis of the first illumination light; and a photosensor for each sample cuvette and disposed on the optical axis of the second light source means for measuring both an optical response from each sample to the first illumination light and the intensity of the transmitted light from each sample.

2. A multichannel optical measuring system according to claim 1; wherein the first single light source includes means for providing the first illumination light as ultraviolet light; and each photosensor includes means for measuring the intensity of light from the sample.

3. A multichannel optical measuring system according to claim 1; further comprising amplifying means for amplifying an output of each photosensor.

4. A multichannel optical measuring system according to claim 3; wherein the amplifying means comprises a plurality of operational amplifiers having amplification factors selected to compensate for background light.

5. A multichannel optical measuring system according to claim 3; further comprising an analog-to-digital converter receptive of an analog output from the amplifying means for converting the analog output to digital output.

6. A multichannel optical measuring system according to claim 5; further comprising computing means receptive of the digital output for measuring and analyzing the digital output.

7. A multichannel optical measuring system according to claim 1; wherein at least one set of optical fibers of the multibranch optical fiber means comprises a non-fluorescent filler surrounding a plurality of quartz optical fibers.

8. A multichannel optical measuring system according to claim 1; wherein at least one measurement sample cuvette comprises a round glass cuvette.

9. A multichannel optical measuring system according to claim 1; further comprising attenuating means for attenuating stray light from the first single light source and for attenuating light due to autofluorescence from the sample cuvette.

10. A multichannel optical measuring system according to claim 1; further comprising interference filtering means for filtering at least one of the first illumination light to provide the first illumination light having a selected wavelength and light received by each photosensor to detect light having a selected wavelength.

11. A multichannel optical measuring system according to claim 1; wherein the second light source means comprises a plurality of light-emitting diodes for illuminating respective sample cuvettes with the second illumination light; and further comprising means for interrupting illumination by the first illumination light; and means for energizing each light-emitting diode at a same time as illumination by the first illumination light is interrupted so as to effect time-series measurement of the optical response from each sample to the first illumination light and the intensity of the transmitted light from each sample.

12. A multichannel optical measuring system for measuring optical responses of samples illuminated by light, comprising: a plurality of measurement sample cuvettes; a first single light source for providing a first illumination light; a plurality of optical fiber sets, each optical fiber set being effective to direct light from the first single light source to illuminate a respective sample cuvette; a plurality of second light sources for illuminating respective sample cuvettes with a second illumination light; and a plurality of photosensors disposed adjacent respective ones of the sample cuvettes on the optical axis of the second light source for measuring light from the sample.

13. A multichannel optical measuring system according to claim 12; wherein the first single light source includes means for providing the first illumination light as ultraviolet light; and the photosensors each include means for measuring the intensity of light from the sample.

14. A multichannel optical measuring system according to claim 13; further comprising amplifying means for amplifying an output of the photosensors.

15. A multichannel optical measuring system according to claim 14; wherein the amplifying means comprises a plurality of operational amplifiers having amplification factors selected to compensate for background light.

16. A multichannel optical measuring system according to claim 14; further comprising an analog-to-digital converter receptive of an analog output from the amplifying means for converting the analog output to digital output.

17. A multichannel optical measuring system according to claim 16; further comprising computing means receptive of the digital output for measuring and analyzing the digital output.

18. A multichannel optical measuring system according to claim 12; further comprising attenuating means for attenuating stray light from the first single light source and for attenuating light due to autofluorescence from the sample cuvette.

19. A multichannel optical measuring system according to claim 12; further comprising interference filtering means for filtering at least one of the first illumination light to provide the first illumination light having a selected wavelength and light received by each photosensor to detect light having a selected wavelength.

20. A multichannel optical measuring system according to claim 12; wherein the plurality of second light sources comprises a plurality of light-emitting diodes for illuminating respective sample cuvettes with the second illumination light; and further comprising means for interrupting illumination by the first illumination light; and means for energizing each light-emitting diode at a same time as illumination by the first illumination light is interrupted so as to effect time-series measurement of the optical response from each sample to the first illumination light and the intensity of the transmitted light from each sample.

* * * * *